United States Patent
Perone

(10) Patent No.: US 7,163,544 B1
(45) Date of Patent: Jan. 16, 2007

(54) AXIS-TRACTION HANDLE WITH A PULL-SENSING GRIP FOR THE OBSTETRICAL FORCEPS

(76) Inventor: Nicola Perone, 8827 Memorial Dr., Houston, TX (US) 77024

(*) Notice: Subject to any disclaimer, the term of this patent is extended or adjusted under 35 U.S.C. 154(b) by 0 days.

(21) Appl. No.: 10/460,830

(22) Filed: Jun. 12, 2003

Related U.S. Application Data

(63) Continuation-in-part of application No. 10/455,910, filed on Jun. 6, 2003, now Pat. No. 7,014,642.

(51) Int. Cl.
*A61B 17/42* (2006.01)

(52) U.S. Cl. .................................................. 606/122

(58) Field of Classification Search ................ 606/119, 606/121, 122, 123, 124, 205, 208, 209, 210, 606/127, 34, 42, 48, 50, 51, 52
See application file for complete search history.

(56) References Cited

U.S. PATENT DOCUMENTS

| | | | | |
|---|---|---|---|---|
| 683,380 | A * | 9/1901 | Cassidy ...................... | 606/122 |
| 3,665,925 | A * | 5/1972 | Dersookian ................. | 606/124 |
| 3,785,381 | A * | 1/1974 | Lower et al. ............... | 606/122 |
| 5,047,046 | A * | 9/1991 | Bodoia ....................... | 606/205 |
| 5,649,934 | A * | 7/1997 | Smeltzer et al. ............ | 606/122 |
| 6,080,106 | A * | 6/2000 | Lloyd et al. ................ | 600/300 |
| 6,210,330 | B1* | 4/2001 | Tepper ....................... | 600/439 |
| 6,402,691 | B1* | 6/2002 | Peddicord et al. .......... | 600/300 |
| 6,409,636 | B1* | 6/2002 | Risso et al. ................. | 482/82 |
| 6,425,899 | B1* | 7/2002 | Biehl ......................... | 606/122 |
| 6,468,284 | B1* | 10/2002 | Wallace ..................... | 606/123 |
| 2002/0193670 | A1* | 12/2002 | Garfield et al. ............ | 600/304 |

OTHER PUBLICATIONS

Bill, A.H.: A New Axis Traction Handle for Solid Blade Forceps. Am. J. Obstet. & Gynecol. 9:606, 1925.
Wylie, B.: Traction in Forceps Deliveries. Am. J. Obstet. & Gynecol. 29:425, 1935.
Baxter, J.: The Obstetrical Forceps: Controlled Axis Traction. J. Obstet. Gynec. Brit. Emp. 53:42, 1946.
Fleming, A.R., Brandeberry, K.R., and Pearse, W.H.: Introduction of a Metric Forceps. Am. J. Obstet. & Gynecol. 78:125, 1959.

* cited by examiner

*Primary Examiner*—Kevin T. Truong
(74) *Attorney, Agent, or Firm*—Arnold & Ferrera, L.L.P.; Raymond Ferrera

(57) ABSTRACT

The invention consists of an axis-traction handle with a pull-sensing grip (4) for the obstetrical forceps, whose object is to reduce the risk of injury to the fetus, caused by excessive traction force during a forceps delivery. The grip contains electronic hardware which include a strain gauge to measure the pull exerted on the axis-traction handle, and thus on the fetal head, during a forceps delivery, a sounder to alert the doctor when the pull exceeds preset safety limits, and a transceiver for the wireless transmission of the pull data to a receiver connected to a lap-top computer with specific software, which generates a graphic representation of such data.

12 Claims, 4 Drawing Sheets

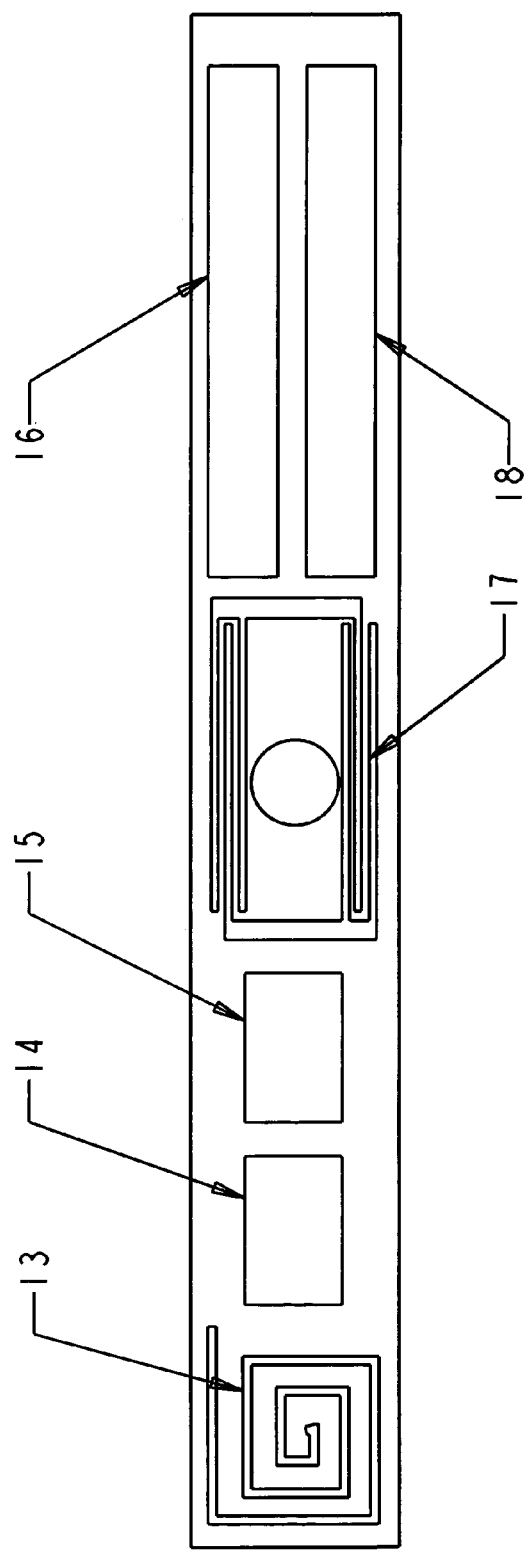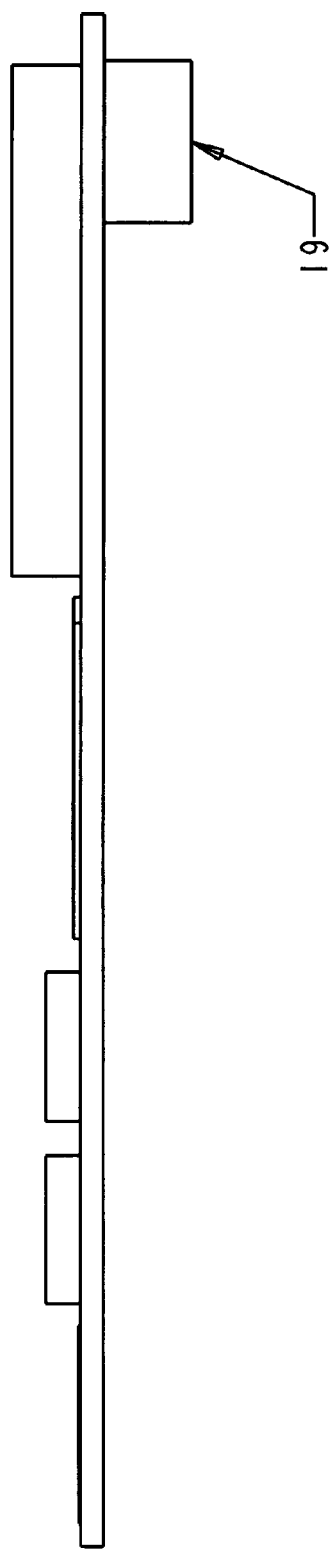
FIG. 4A
FIG. 4B

AXIS-TRACTION HANDLE WITH A PULL-SENSING GRIP FOR THE OBSTETRICAL FORCEPS

CROSS-REFERENCE TO RELATED APPLICATIONS

This application is a continuation-in-part of U.S. patent application Ser. No. 10/455,910, filed Jun. 6, 2003, now U.S. Pat. No. 7,014,642.

FIELD OF THE INVENTION

This invention pertains to devices for assisting in the delivery of a baby. Specifically, the present invention relates to an axis-traction handle with a pull-sensing grip for the obstetrical forceps, containing electronic hardware whose purpose is to measure the pull exerted on the handle, and thus on the fetal head, during a forceps delivery, to alert the doctor when such a pull exceeds preset safety limits, and to enable the wireless transmission of the pull data to a receiver connected with a lap-top computer with specific software.

BACKGROUND OF THE INVENTION

Obstetrical forceps are medical instruments comprised of two blades (i.e. the fetal head engaging portions), each connected to a handle by a shank, with a sliding lock between the handle and the shank. The forceps typically grasp the fetal head in a tong-like manner and are used for assisting in the delivery of a baby. When needed, they can be a valuable medical tool to shorten or end the second (expulsion of the fetus) stage of labor, whenever to do so is in the best interest of the mother or the fetus.

In 1925 A. H. Bill introduced the axis-traction handle for the obstetrical forceps, which was widely accepted and soon became an integral part of the instrumental delivery armamentarium available in every delivery room.

The Bill axis-traction handle consists of a claw, which is applied to the forceps handle finger guards just like two fingers would grasp them, a vertical rod connecting, through a movable joint, the claw to a horizontal traction rod, which, in turn is attached to a handle grip. The purpose of the Bill axis-traction handle is to increase the accuracy of traction, i.e., to allow the physician to direct the traction away from the symphysis into the axis of the pelvis, which is the one of least resistance, thus, reducing the amount of traction necessary for a forceps delivery.

Regrettably, even when the axis-traction principle is strictly adhered to, the possibility of maternal and/or fetal injury, secondary to excessive pull, remains a reality. In fact, when to desist from further extractive efforts is left to the judgment and courage of the obstetrician.

To be sure, the medical literature contains several reports of attempts made to modify the Bill axis-traction handle in order to be able to measure the pull applied during a forceps delivery, and thus, reduce the risk of injury to the fetus. As early as 1935, B. Wylie reported a modification of the Bill axis-traction handle with the insertion of a spring mechanism to measure the amount of traction during a delivery. A similar spring mechanism was described in 1946 by J. Baxter. In 1959 A. R. Fleming et al. reported a further modification consisting in the placement of strain gauges on the vertical rod of the handle, connected to a recording instrument.

The above modifications, while useful for research purposes, have not, however, gained clinical acceptance, possibly because they require calibration, have cumbersome cable connections, and pose problems with sterilization.

Accordingly, there is a need for an improved axis-traction handle for the obstetrical forceps, that can measure the pull exerted on the handle, and thus on the fetal head, during a forceps delivery, without the constraints and design drawbacks seen in the prior art and described above.

SUMMARY OF THE INVENTION

The invention consists of an axis-traction handle with a pull-sensing grip for the obstetrical forceps, whose object is to reduce the risk of injury to the fetus, caused by excessive pull during a forceps delivery. The grip contains electronic hardware whose purpose is to measure the pull exerted on the axis-traction handle, and thus on the fetal head, during a forceps delivery, to set off an audible signal when such a pull exceeds preset safety limits, and to transmit in a wireless fashion, the pull data to a receiver connected with a lap-top computer.

A novel feature of this invention is the easy adaptability of the axis-traction handle with the pull-sensing grip to almost any forceps, thus making unnecessary to discard one's favorite forceps. Another novel feature is the elimination of cumbersome cable connections between the strain gauge and the sounder, and between the transceiver and the receiver, which can interfere with the forceps application. Still another novel feature of this invention is the graphic representation of the pull exerted on the axis-traction handle throughout a forceps delivery, useful for research purposes or in case of medical malpractice litigation. A further feature of this invention is that the axis-traction handle with the pull-sensing grip can be either disposed after a single use, or it can be easily sterilized and reused, without significant impact on materials or functionality.

The foregoing has outlined rather broadly the features and technical advantages of the present invention so that the detailed description of the invention that follows may be better understood. Additional features and advantages of the invention will be described hereinafter, which form the subject of the invention. It should be appreciated by those skilled in the art that the conception and the specific embodiments disclosed might be readily used as a basis for modifying or designing other pull-sensing grips for the axis-traction handle for carrying out the same purposes of the present invention. It should also be realized by those skilled in the art that such equivalent constructions do not depart from the spirit and scope of the invention as set forth herein.

BRIEF DESCRIPTION OF THE DRAWINGS

The accompanying drawings, which are incorporated in and form a part of the specification, illustrate the embodiments of the present invention, and, together with the description, serve to explain the principles of the invention. In the drawings:

FIGS. 4A and 4B are a top and side view of a printed circuit board of the present invention, showing a radio frequency antenna, a transceiver chip, a microprocessor chip, a field coil recharger, a strain gauge, a rechargeable battery, and a sounder.

It is to be noted that the drawings illustrate only typical embodiments of the invention and are therefore not to be considered limiting of its scope, for the invention will admit to other equally effective embodiments.

DETAILED DESCRIPTION OF THE INVENTION

Figure 1:
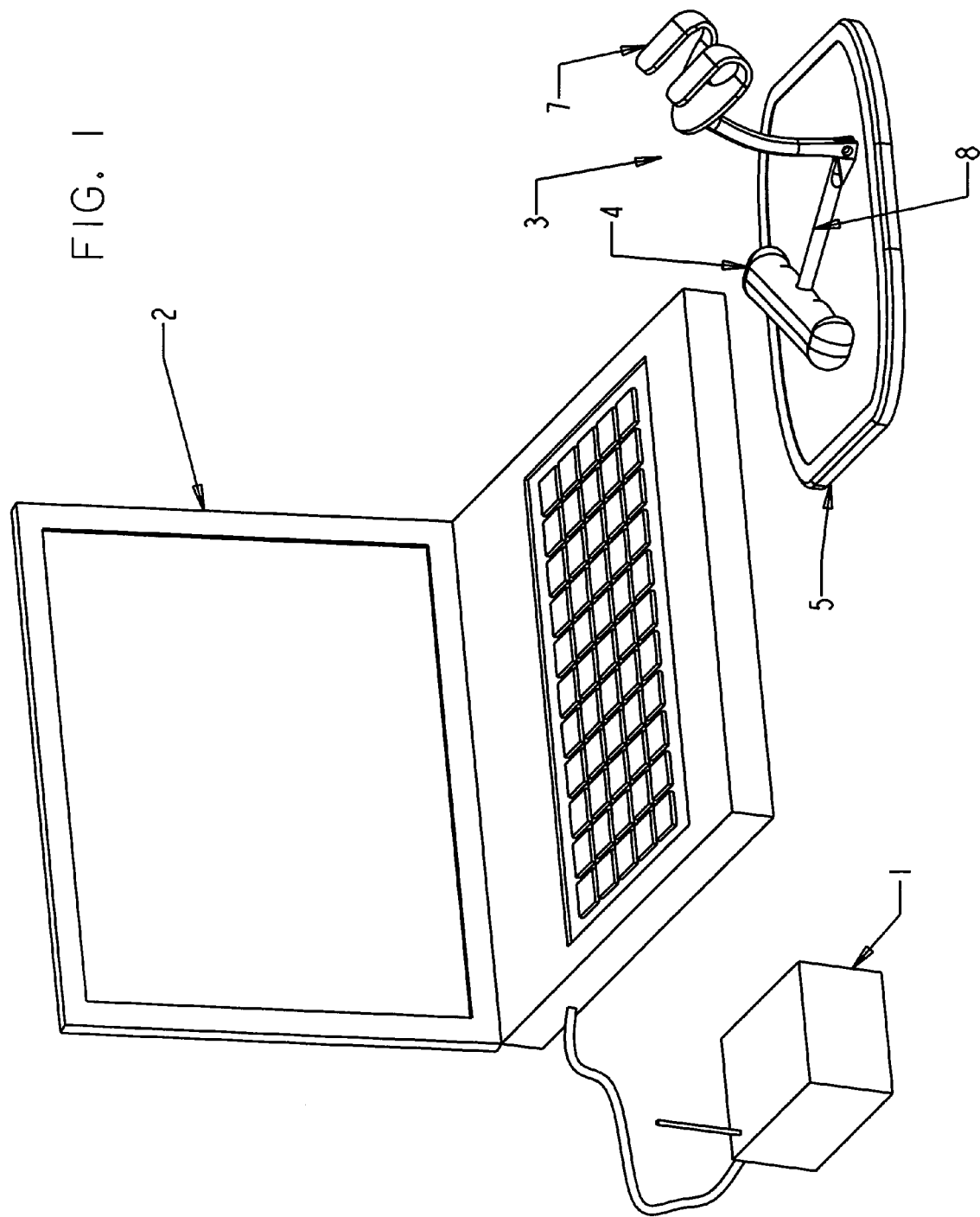
FIG. 1 shows the axis-traction handle with the electronic grip assembly in place, resting on a recharge pad, and a radio receiver connected to a lap-top computer.
Figure 2:
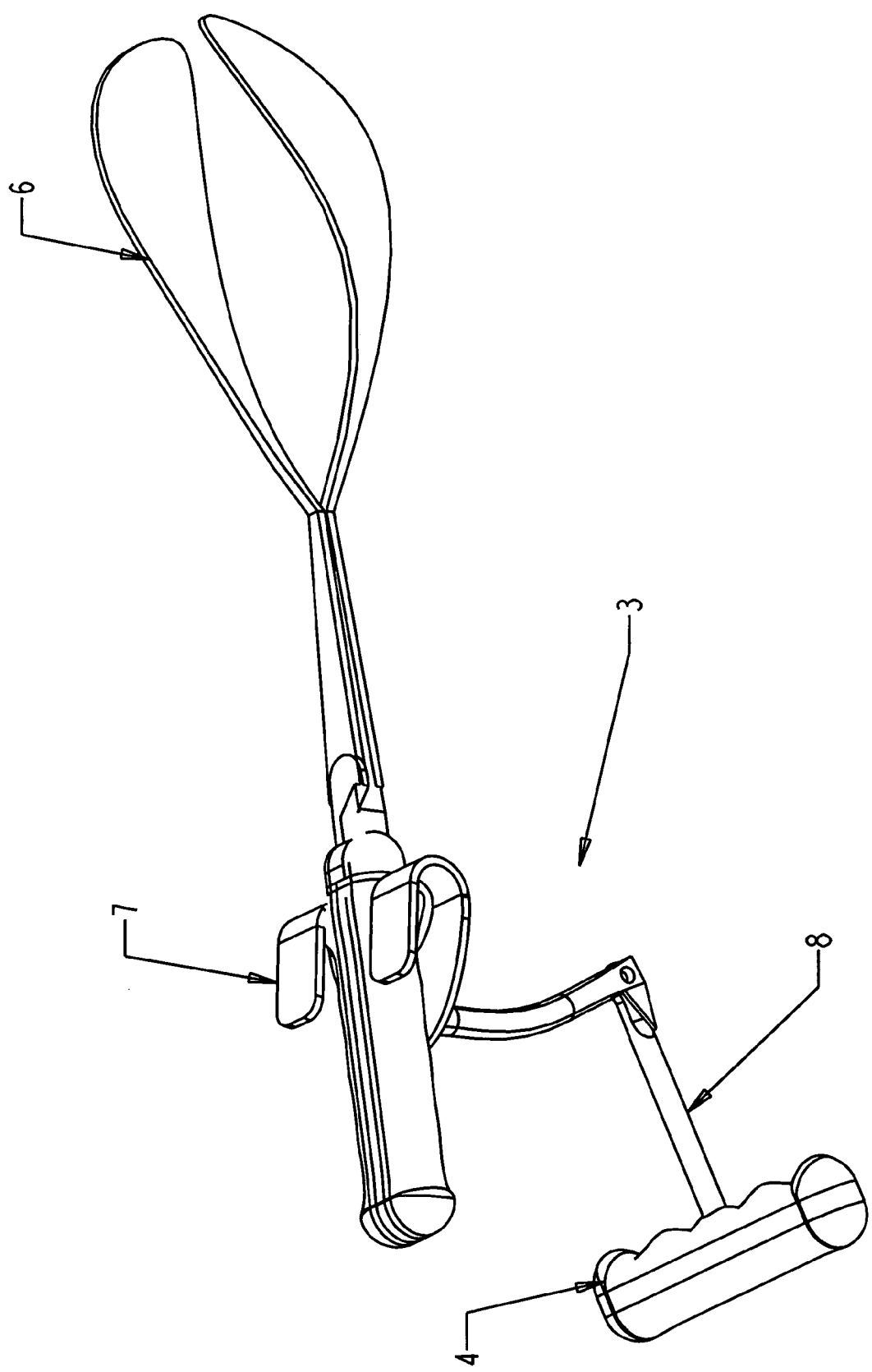
FIG. 2 shows the axis-traction handle with the electronic grip assembly attached to the finger guards of an Elliot type forceps (Tucker-McLane)

Turning now to FIG. 1, there is shown the axis-traction handle (3) with the pull-sensing grip (4) for the obstetrical forceps. The grip assembly (4) rests on a recharging pad (5) used to inductively recharge the power supply or batteries housed within the handle grip (4). As also seen in FIG. 1, a radio receiver (1) is connected with a lap-top computer (2), which displays and records the pull data transmitted by the grip assembly and generates a graphic recording of said data, which can be stored, analyzed, processed, or otherwise made part of the patient's hospital medical record. FIG. 2 shows the axis-traction handle with the electronic grip assembly (4) attached to the finger guards of an Elliot type forceps (Tucker-McLane) (6).

While many different types of forceps made of different materials have been described and developed throughout time, they consist principally of the following four major components:

(A) Blades: Each blade has two curves. A pelvic curve that follows the direction of the birth canal, and a cephalic curve that fits the shape of the baby's head. The blades can be oval or elliptical and can be fenestrated or solid, with smooth surfaces and edges in order to reduce damage to the soft tissues when applied to the fetal head.

(B) Shanks: These connect the blades to the handles and provide the length of the device. They are either parallel or crossing and are often made of stainless steel.

(C) Lock: Many different types have been designed. The lock is the type of articulation between the shanks.

(D) Handles: These are where the doctor holds the forceps device and applies traction the fetal head. As shown in FIG. 2, the claw (7) of the axis-traction handle (3) is attached to the handle finger guards of the forceps, just like two fingers would grasp them, to provide axis traction. FIG. 2 also shows the horizontal traction rod (8).

Figure 3:
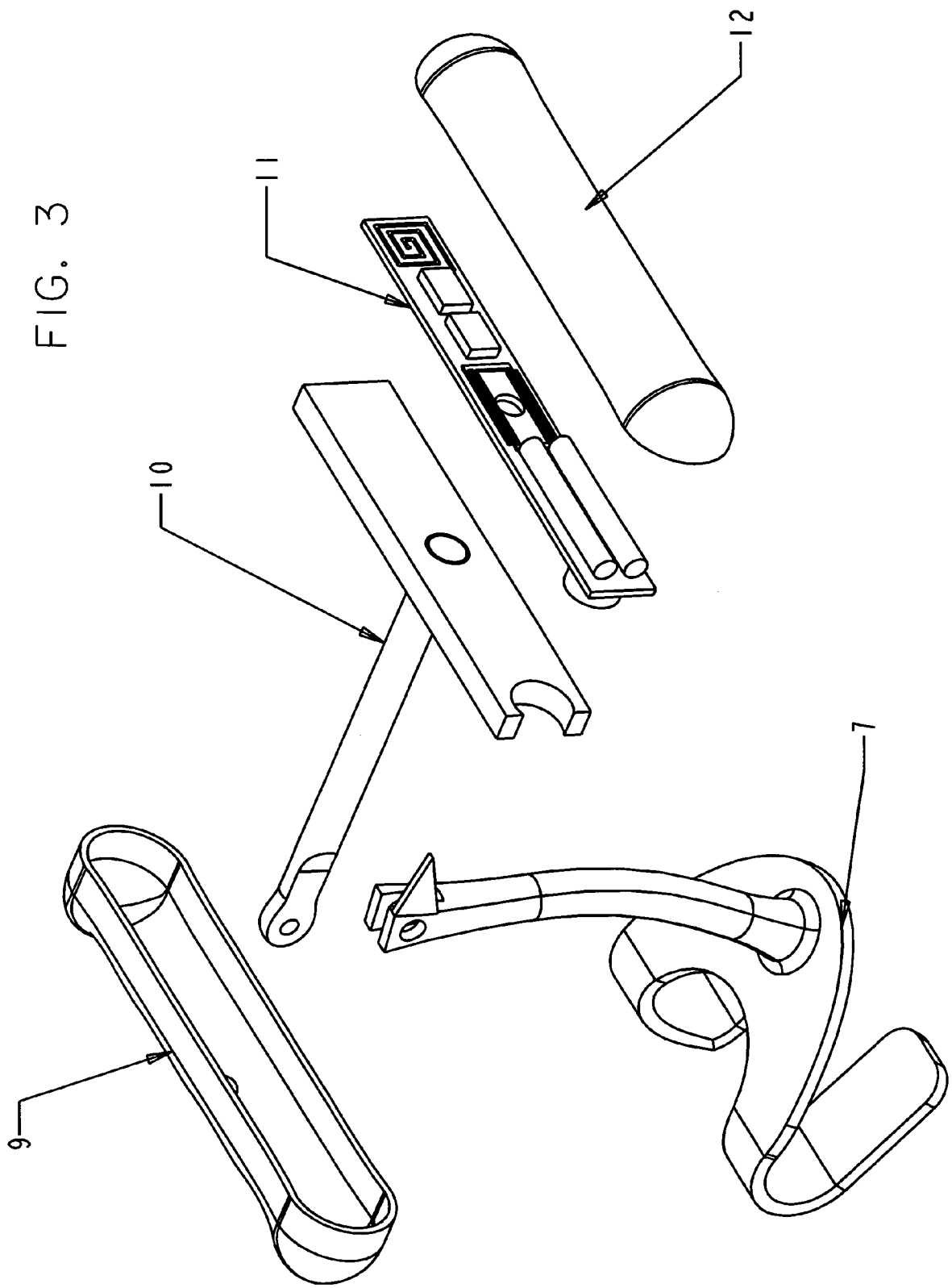
FIG. 3 is an exploded perspective view of the grip assembly of the present invention with a structural T-handle, a printed circuit board, and a claw with a vertical rod.

Turning now to FIG. 3, the grip is made up of a top (9) and bottom (12) plastic housing, containing a structural T-handle (10) and a printed circuit board (PCB) assembly (11), whose purpose is to measure the pull applied to the grip, to transmit the pull data, and to control power envelope. If desired, the top (9) and bottom (12) plastic housing can be provided with the usual contoured finger gripping surfaces for facilitating gripping by hand. When assembled, the circuit board (11) is potted into the plastic housing using known manufacturing techniques.

As seen in FIGS. 4A and 4B, the PCB assembly consists of a strain gauge (17), a microprocessor chip (15), a transceiver chip (14), a rechargeable battery (18), a field coil recharger (16), a sounder (19), and a radio frequency antenna (13).

In particular, the strain gauge (17) measures the pull applied to the handle grip. While any range of traction force may be measured, the typical range force is 0 to 100 pounds of force in a delivery. While there are several methods of measuring strain, the most common is with a strain gauge, such as a resistive gauge. When force is applied to a structure, the length of the structure changes. Strain is the ratio of this change in dimension to the original, and strain gauges are used to measure it. As the strain gauge is glued to the structure, any distortion will also cause a distortion of the strain gauge. The gauge contains semi-conducting material and the distortion therefore results in a change in its resistance. By measuring this change in resistance, one can measure the strain. As such, a strain gauge's electrical resistance varies in proportion to the amount of strain placed on it.

The microprocessor chip (15) controls the functions of the grip assembly. While many different microprocessors known in the art can be used, the preferred chip is an 8-bit chip with sufficient RAM date storage.

The transceiver chip (14) controls radio communications between the grip assembly and radio receiver (1). The preferred transceiver chip is a digital chip that can transmit the desired strain gauge data to the receiver. While any analog or digital radio frequency (RF) or infrared frequency (IF) spectrum communication system is contemplated, any kind of wireless system now known (or to be known) in the art can be used with this device, including Bluetooth wireless technology.

The rechargeable battery (18) provides power during forceps use. As is known to those skilled in the art, popular rechargeable batteries include NiCd and NiMH batteries. If desired, a disposable, non-rechargeable battery such as an alkaline battery can be used.

The field coil recharger (16) provides recharging power to the battery (18) when the axis-traction handle grip assembly rests on the recharging pad (5). The preferred field coil recharger that is used is known as "near-field" field coil recharger.

The sounder or speaker (19) creates an audible warning alarm when the pull on the axis-traction handle reaches a preset safety limit. How much pull to be applied to the axis-traction handle in order to complete a forceps delivery depends on such factors as the number of babies previously borne by the mother and the size and weight of the baby. Of course, instead of an audible alarm signal, the device could be constructed to provide a visual alarm signal or other signal. Because of the size of the device, a micro-speaker is preferred.

The radio frequency antenna (13) relates data between the handle grip assembly and the receiver. In general, any kind of radio frequency antenna system for a wireless infrastructure can be used, such as a digital high frequency antenna.

The radio receiver (1) is connected with a lap-top computer (2), which records the pull data transmitted by the grip assembly and generates a graphic recording of said data, which can be made part of the patient's hospital medical record. Through the wireless technology described herein, the doctor is able to accurately and safely gauge the amount of pull exerted on the axis-traction handle, and thus on the baby's head, by the forceps, thereby preventing damage to the baby and to the mother.

As described herein, the present invention obviates the problems of the prior art by providing a grip for the axis-traction handle, containing all the electronic hardware necessary to accurately measure the pull applied to the axis-traction handle during a forceps delivery, to alert in real-time the doctor when such a pull exceeds preset safety limits, and to enable the wireless transmission of the pull data to a receiver connected with a lap-top computer. In this fashion a graphic representation can be generated of the pull exerted on the axis-traction handle during a forceps delivery, which can be presented in case of medical malpractice litigation, as evidence that safety limits were not exceeded.

In addition, as far as sterilization is concerned, the axis-traction handle with the electronic grip assembly can be provided already sterile and disposed after a single use, or, in its re-usable version, it can be easily sterilized without any damage to the electronic hardware, either through a low temperature sterilization process (such as the STIRRAD method), or, alternatively, by immersion in a sterilizing solution (such as CIDEX). In fact, the printed circuit board is encapsulated within the plastic grip with epoxy compound, thus it is impervious to immersion in a liquid disinfectant.

Although the present invention and its advantages have been described in detail, it should be understood that various changes, substitutions, and alterations could be made herein without departing from the spirit and scope of the invention as defined by the appended claims.

What is claimed is:

1. An obstetrical forceps system for assisting in the delivery of a fetus, said system comprising:
    an obstetrical forceps;
    an axis-traction handle with a pull-sensing grip detachably connected to said obstetrical forceps;
    a means for electronically measuring the magnitude of extraction forces exerted on said grip, and thus the fetal head, during a forceps delivery, wherein the measuring means is disposed within said grip;
    a means for transmitting data regarding measured extraction forces; and
    a means for receiving said data regarding measured extraction forces.

2. The system of claim 1, wherein said means for electronically measuring the magnitude of extraction forces exerted on said grip, and thus on the fetal head, further comprises a strain gauge.

3. The system of claim 1, wherein said means for transmitting data regarding measured extraction forces further comprises a transmitter.

4. The of claim 1, wherein said means for receiving said data regarding measured extraction forces further comprises a receiver.

5. The system of claim 1, further comprising a means for graphically representing said data regarding measured extraction forces.

6. The system of claim 1, further comprising a means for generating an alarm when said data regarding measured extraction forces indicates said extraction forces have exceeded predetermined safety limits.

7. The system of claim 6, wherein said means for generating an alarm further comprises a speaker.

8. The system of claim 7, wherein said speaker is disposed within said pull-sensing grip.

9. An axis-traction handle for use with obstetrical forceps, said axis-traction handle comprising:
    a claw, wherein said claw attaches to the handle finger guards of the obstetrical forceps;
    a horizontal traction rod, said rod being attached to said claw on one end and comprising a structural T-handle on the other end; and
    a pull-sensing grip, wherein said grip contains the structural T-handle of said horizontal traction rod, and
    a means for electronically measuring the magnitude of extraction forces exerted on said grip, and thus the fetal head, during a forceps delivery, wherein the measuring means is disposed within said grip.

10. The axis-traction handle of claim 9, wherein said pull-sensing grip further comprises:
    a means for generating an alarm when said data regarding measured extraction forces indicates said extraction forces have exceeded predetermined safety limits.

11. The axis-traction handle of claim 10, wherein said means for generating an alarm when said data regarding measured extraction forces indicates said extraction forces have exceeded predetermined safety limits further comprises a speaker.

12. The axis-traction handle of claim 9 wherein said means for electronically measuring the magnitude of extraction forces exerted on the structural T-handle during a forceps delivery further comprises a strain gage.

* * * * *